(12) United States Patent
Roehl et al.

(10) Patent No.: US 7,455,062 B2
(45) Date of Patent: Nov. 25, 2008

(54) MODULAR NITRIC OXIDE DELIVERY DEVICE

(75) Inventors: Robin L. Roehl, Janesville, WI (US); Craig R. Tolmie, Stoughton, WI (US)

(73) Assignee: The General Electric Company, Schenectady, NY (US)

( * ) Notice: Subject to any disclaimer, the term of this patent is extended or adjusted under 35 U.S.C. 154(b) by 512 days.

(21) Appl. No.: 11/201,053

(22) Filed: Aug. 10, 2005

(65) Prior Publication Data
US 2007/0034208 A1 Feb. 15, 2007

(51) Int. Cl.
*A61M 16/00* (2006.01)
*A61M 16/20* (2006.01)
*A61M 16/10* (2006.01)
*A61M 16/14* (2006.01)

(52) U.S. Cl. ............................. 128/204.21; 128/202.27; 128/203.12; 128/203.25; 128/204.18; 128/205.24

(58) Field of Classification Search ............ 128/204.21, 128/200.24, 202.22, 202.27, 203.12, 203.14, 128/203.25, 204.18, 204.22, 204.26, 205.11, 128/205.18, 205.24
See application file for complete search history.

(56) References Cited

U.S. PATENT DOCUMENTS

| | | | | |
|---|---|---|---|---|
| 5,522,381 A | * | 6/1996 | Olsson et al. | 128/203.12 |
| 5,558,083 A | | 9/1996 | Bathe et al. | |
| 5,699,790 A | * | 12/1997 | Bathe et al. | 128/204.22 |
| 5,839,433 A | * | 11/1998 | Higenbottam | 128/204.21 |
| 6,032,667 A | * | 3/2000 | Heinonen | 128/205.24 |
| 6,089,229 A | | 7/2000 | Bathe et al. | |
| 6,109,260 A | | 8/2000 | Bathe | |
| 6,125,846 A | | 10/2000 | Bath et al. | |
| 6,164,276 A | | 12/2000 | Bathe et al. | |
| 6,279,574 B1 | * | 8/2001 | Richardson et al. | 128/204.18 |

(Continued)

FOREIGN PATENT DOCUMENTS

WO WO 9844976 A1 * 10/1998

(Continued)

*Primary Examiner*—Justine R Yu
*Assistant Examiner*—Clinton Ostrup
(74) *Attorney, Agent, or Firm*—Andrus, Sceales, Starke & Sawall, LLP

(57) ABSTRACT

A nitric oxide delivery device is provided that can be formed as a module that is insertable in a mating equipment bay in a gas delivery system found in one location, removed and used in conjunction with a transport gas delivery system when the patient is transported, and thereafter inserted in the equipment bay of a gas delivery system located at a second location. In a preferred embodiment, the device includes a housing having an NO supply port, an NO delivery port, a flow sensor port, and a conduit pneumatically connected to the NO supply port and the NO delivery port. A selector valve is positioned in the conduit and selectively moves between a first position wherein the NO supply port is pneumatically connected to the NO delivery port and a second position wherein the NO delivery port is pneumatically connected to a temporary supply of NO. The housing further has a power supply port, a temporary power source and a switch being selectively movable between a first position wherein power is provided to the NO delivery device via the power supply port and a second position wherein power is provided to the device from the temporary power source.

17 Claims, 4 Drawing Sheets

U.S. PATENT DOCUMENTS

| | | | |
|---|---|---|---|
| 6,390,091 B1 * | 5/2002 | Banner et al. | 128/204.21 |
| 6,474,333 B1 * | 11/2002 | Heinonen | 128/203.12 |
| 6,581,592 B1 | 6/2003 | Bathe et al. | |
| 6,782,888 B1 * | 8/2004 | Friberg et al. | 128/204.18 |
| 7,219,666 B2 * | 5/2007 | Friberg et al. | 128/204.18 |
| 2002/0178783 A1 * | 12/2002 | Miller et al. | 73/23.2 |
| 2005/0000519 A1 * | 1/2005 | Friberg et al. | 128/204.18 |
| 2005/0172966 A1 * | 8/2005 | Blaise et al. | 128/204.21 |

FOREIGN PATENT DOCUMENTS

WO      WO 0059566 A1 * 10/2000

* cited by examiner

MODULAR NITRIC OXIDE DELIVERY DEVICE

BACKGROUND OF THE INVENTION

The present invention relates to a device for delivering nitric oxide into the breathing gases of a patient that is modular in nature. The device may be used to advantage to maintain nitric oxide therapy when a patient is being transported from one location to another location.

Nitric oxide (NO) is a gas that, when inhaled, acts to dilate blood vessels in the lungs, improving oxygenation of the blood and reducing pulmonary hypertension. For this purpose, the nitric oxide is provided in the inspiratory breathing gases for the patient. The dosages of nitric oxide are small, typically 100 parts per million (ppm) or less.

In many cases, the inspiratory breathing gases for the patient will be provided by a gas delivery system such as a mechanical ventilator. U.S. Pat. No. 5,558,083 shows apparatus for administering NO into the inspiratory breathing gases provided by a mechanical ventilator. The apparatus includes a connection to a NO supply conduit inserted in the inspiratory limb of a patient breathing circuit connected to the ventilator. The NO supply conduit is connected through a controllable metering valve to a supply of NO containing gas. Flow sensors are provided in the NO supply conduit and in the inspiratory limb upstream of the NO supply conduit connection. The flow sensors are connected to a control that operates the metering valve based on the dosage of NO desired for the patient and the gas flows sensed by the concentration sensor. An analytical gas flow sensor is provided downstream of the NO supply conduit connection in the patient breathing circuit to analyze properties of the inspiratory breathing gases being supplied to the patient. The apparatus of the '083 patent provides a generally continuous flow of NO containing gas during the supply of breathing gases to the patient. It is also possible to provide a discrete pulse of NO containing gas at a predetermined time in the inspiratory phase of the patient's breathing cycle.

In a commercial embodiment, NO delivery apparatus of the type described above is typically available as a stand alone unit that is used in conjunction with a breathing gas delivery system when NO therapy is desired for a patient. For this purpose, the breathing gas flow sensor, the nitric oxide supply conduit connection, and the gas analyzer sampling port may be provided in a common housing that can be inserted in the inspiratory limb of the breathing circuit. For best performance, the gas analyzer sample part is placed at a distance from the NO injection point to allow for proper gas mixing. Also, the gas sample point is normally positioned close to the inspiratory side of the wye connector to most accurately sense the level of $NO_2$ being produced. The commercial embodiment provides the advantage of allowing the apparatus to be used with a variety of different breathing gas delivery systems without being restricted to a particular model or to the products of a particular manufacturer.

However, the stand alone unit tends to be somewhat bulky. It is preferable to keep the NO supply conduit short and to administer the NO into the inspiratory breathing gases close to the patient to avoid/limit a reaction between the NO and oxygen in the breathing gases that leads to the production of toxic nitrogen dioxide in the breathing gases. This often means that the NO delivery apparatus is proximate to the patient and is in the way of other apparatus or attending patient caregivers. Also, with such apparatus, it may be difficult to maintain NO therapy when transporting a patient from one location to another as, for example, from an intensive care unit to a regular hospital room.

SUMMARY OF THE PRESENT INVENTION

The present invention addresses the foregoing problems by providing a NO delivery device that is compact in nature, thereby to facilitate continuance of NO therapy when a patient is being moved from one location to another.

The NO delivery device may be formed as a module that can be inserted in a mating equipment bay in a gas delivery system found in one location, removed and used in conjunction with a transport gas delivery system when the patient is being transported, and thereafter inserted in the equipment bay of a gas delivery system located at a second location.

DETAILED DESCRIPTION OF THE PREFERRED EMBODIMENTS

Figure 1:
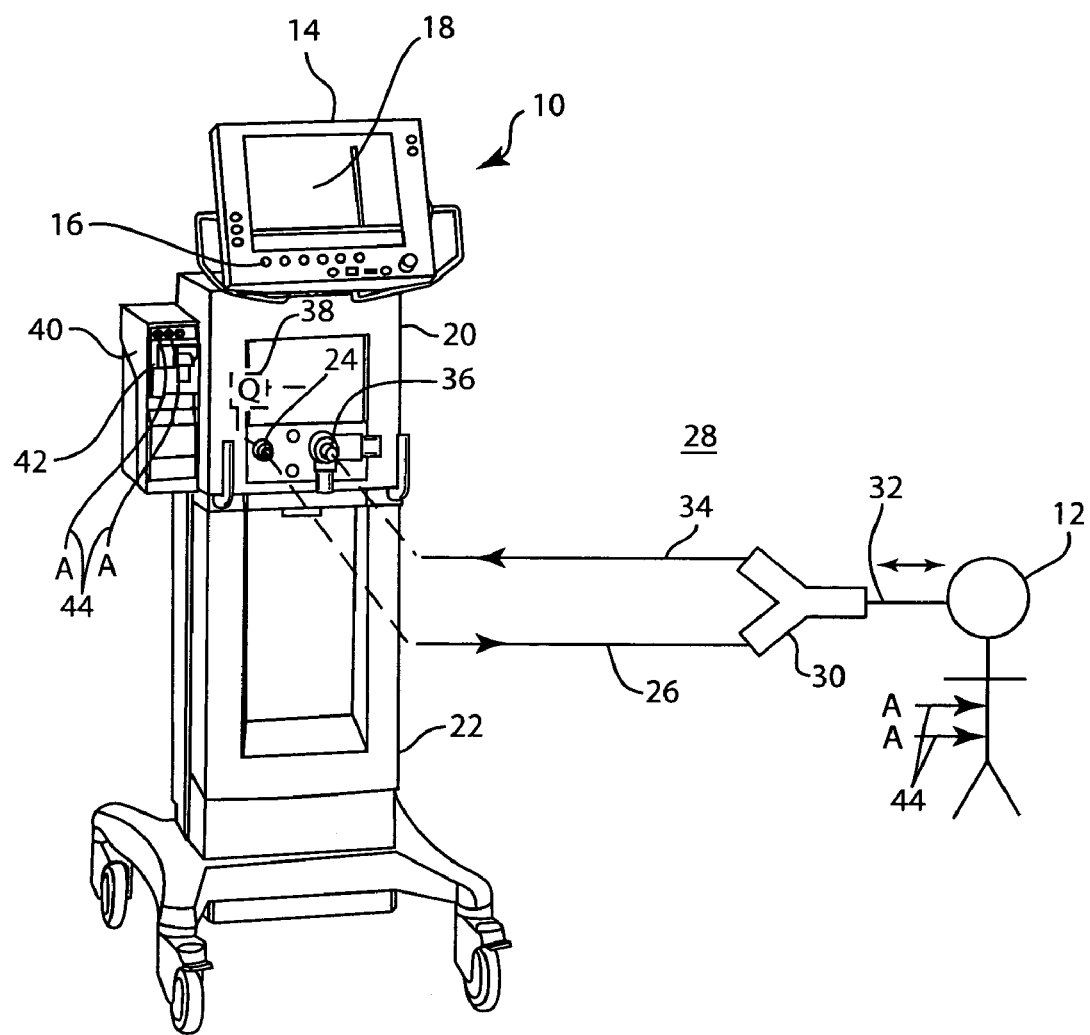
FIG. 1 is a perspective view of a breathing gas delivery system with which the modular NO delivery device of the present invention may be utilized.

FIG. 1 shows a patient breathing gas delivery system 10 with which the modular nitric oxide delivery device of the present invention may be utilized. Breathing gas delivery system 10 may comprise a mechanical ventilator for providing breathing gases to patient 12. Breathing gas delivery system 10 includes a user interface 14 that allows a clinician to establish the operating parameters for the gas delivery system, such as breath rate, tidal volume, minute volume, inspiratory/expiratory (I:E) ratio, breathing gas pressures, and the like. User interface 14 can also be used to set NO concentrations and display NO and $NO_2$ concentrations. These procedures may be carried out using data entry controls 16. User interface 14 also includes screen 18 for providing a visual display of the operation of breathing gas delivery system 10 and the physiological functioning of patient 12.

The pneumatic and mechanical portions of breathing gas delivery system 10 could be contained in housing 20 which may be mounted on wheeled carriage 22 to facilitate moving the gas delivery system into proximity with patient 12.

Breathing gas delivery system 10 includes an inspiratory port 24 connected to inspiratory limb 26 of breathing circuit 28. Inspiratory limb 26 is connected through wye-connector 30 to patient limb 32 that provides the inspiratory breathing gases to patient 12 through a face mask, endotracheal tube, and the like. Patient limb 32, also receives the expiratory breathing gases of patient 12 and supplies them through wye-connector 30 to expiratory limb 34 of breathing circuit 28. Expiratory limb 34 is connected to expiratory port 36 of breathing gas delivery system 10. Breathing gas delivery system 10 includes appropriate check valves to carry out the flow of breathing gases in the manner described above. Among the sensors contained in breathing gas delivery system 10 is flow sensor 38 for measuring the flow of breathing gases in inspiratory limb 26.

Breathing gas delivery system 10 includes modular equipment bay rack 40. In a typical application for breathing gas delivery system 10, the modules in modular equipment bay rack 40 comprise patient monitoring modules that can be selectively inserted in the rack, depending on the parameters of the patient to be monitored. To this end, the modules include patient leads 44 connected to patient 12. Typical modules 42 may include one for carrying out hemodynamic measurements, such as non-invasive blood pressure measurement, blood oxygen measurement, and the like; an electrocardiograph module for obtaining electrocardiographic data; an electroencephalographic module for obtaining EEG data; and a gas monitoring module for measuring breathing gas components such as carbon dioxide, oxygen, nitric oxide, and anesthetic agents.

Figure 2:
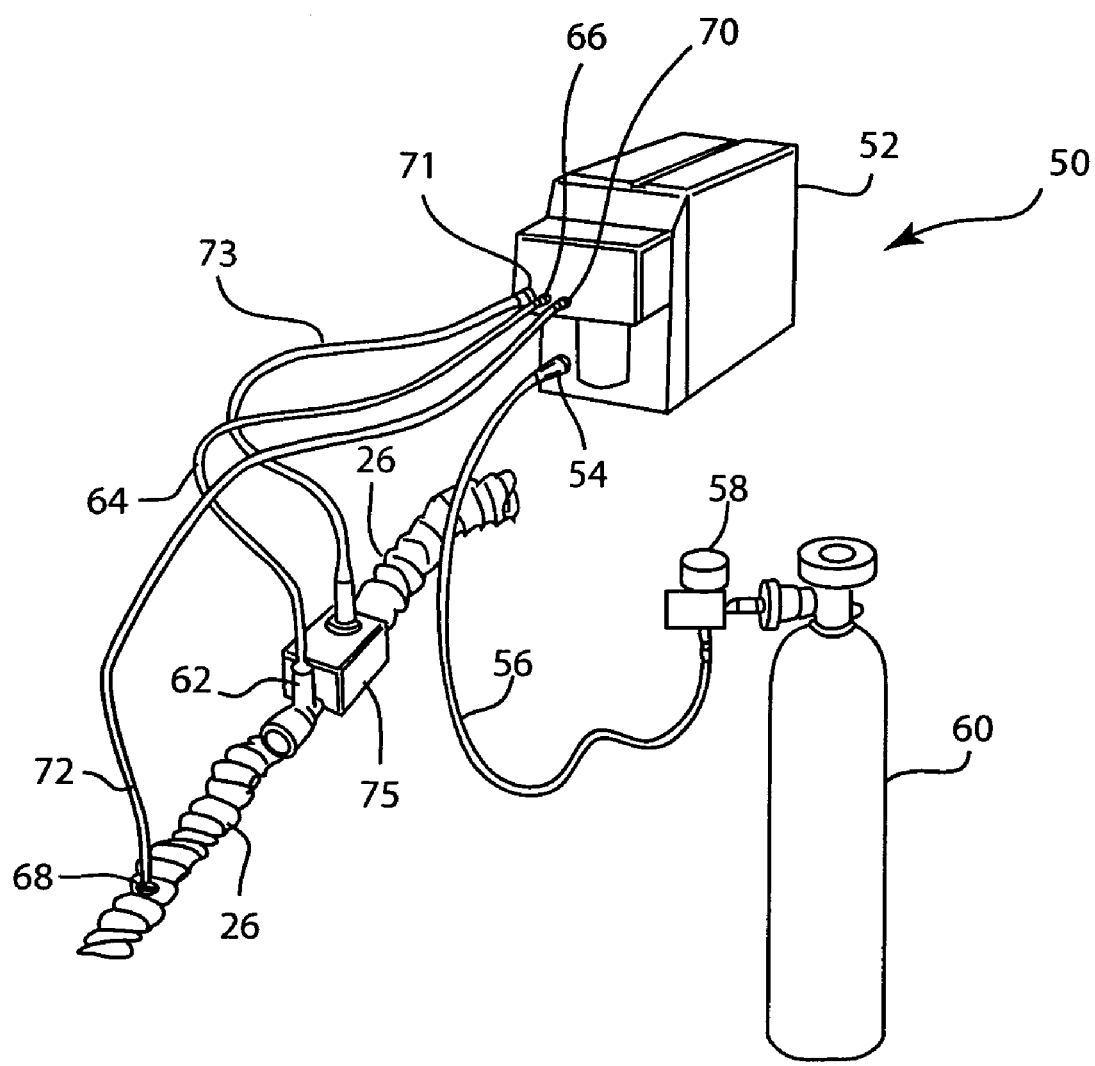
FIG. 2 is a perspective view of the modular NO delivery device of the present invention.

FIG. 2 shows modular NO delivery device 50 of the present invention. Modular delivery device 50 includes a housing 52 of a size suitable for placing in modular equipment bay rack 40 of breathing gas delivery system 10. Modular equipment bay rack 40 may be suitable for receiving modules that are of a single standard width or a double standard width. It is presently contemplated that module 50 would be of a double width with respect to the bays in rack 40. In FIG. 1, modular NO delivery device 50 is inserted in the lower bay of rack 40.

Modular NO delivery device 50 includes a connector 54 for connection to NO supply line 56 connected through pressure regulator 58 to a source of NO containing gas, such as tank 60. Tank 60 typically contains NO in an inert diluent gas, such as nitrogen.

In the embodiment of the invention shown in FIG. 2, NO delivery device includes NO injection element 75 that may be inserted at an appropriate location in inspiratory limb 26, as shown in FIG. 2. Injection point 62 is connected to NO delivery device 50 by NO delivery line 64 connected to NO supply port 66 of delivery device 50. A flow signal can be collected from injection element 75 via flow signal line 73, which is connected to the NO delivery device 50 at connection 71. In addition, an optional gas sampling port 68 can be located downstream of the point of NO injection to sense characteristics of the inspiratory breathing gases in inspiratory limb 26 and to allow for adequate blending prior to sampling. Sampling port 68 is connected to modular delivery device 50 at connection 70 by sampling line 72.

Figure 3:
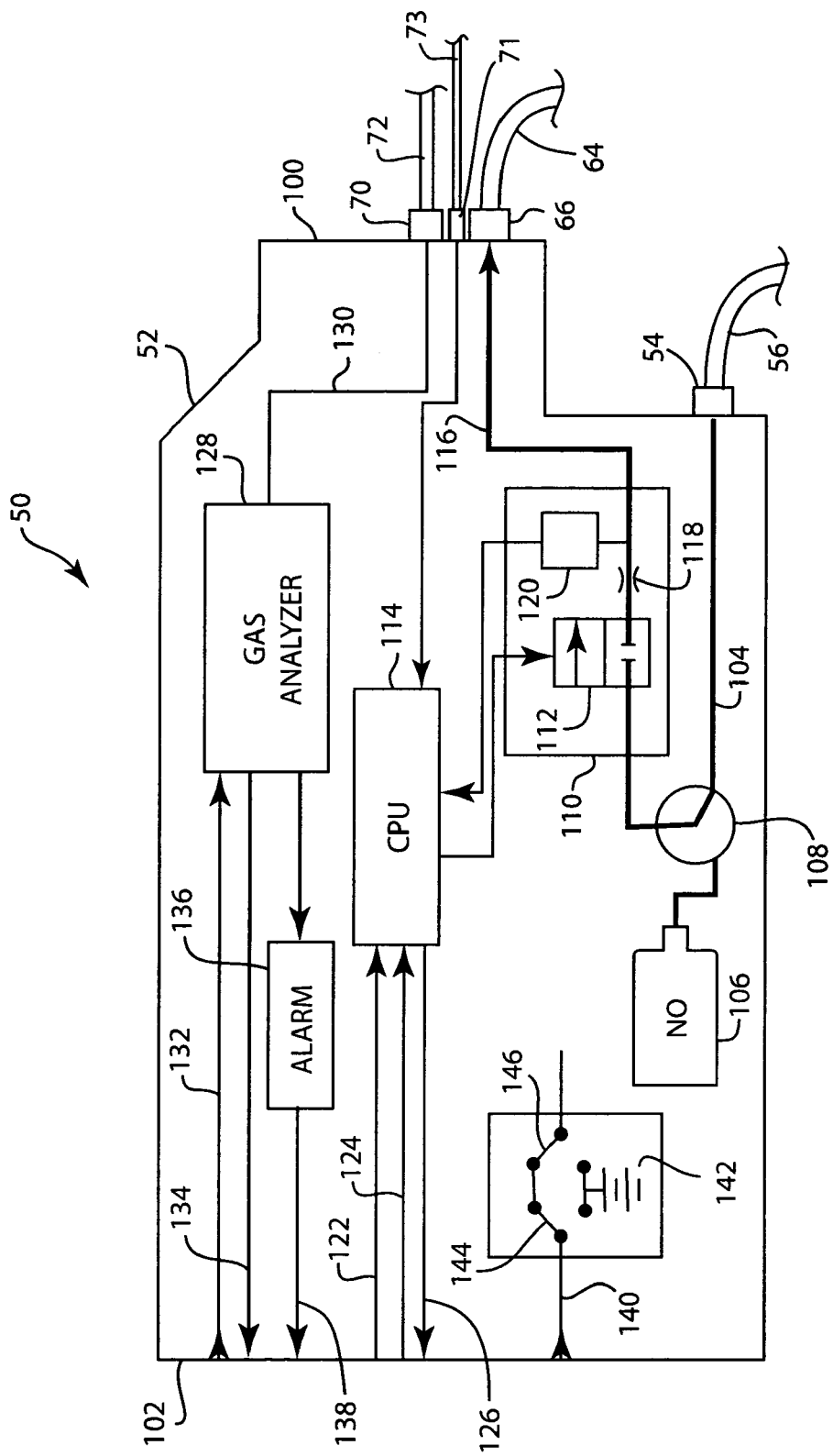
FIG. 3 is a generally schematic showing of the construction of one embodiment of the modular NO delivery device of the present invention.

FIG. 3 shows the components of modular NO delivery device 50. Housing 52 for delivery device 50 has connectors 54, 66, 70, and 71 for NO supply line 56, NO delivery line 64, sampling line 72, and flow signal line 73, respectively, on the surface 100 that is exposed when the module is inserted in modular equipment bay rack 40. Surface 102 of housing 52 contains a plurality of connectors that mate with corresponding connectors in rack 40 when delivery device 50 is inserted in the rack.

NO supply line 56 is connected to conduit 104 in the module. Module 50 may contain a small supply of NO gas 106 for use during the period of time in which patient 12 is being transported. More likely however, the small supply of NO gas 106 comprises a separate container or cylinder that is externally connected to the module 50. Selector valve 108 is connected to a selected one of conduit 104 or NO supply 106 to provide nitric oxide gas to NO dosing means 110. Dosing means 110 contains flow control valve 112. Valve 112 can be opened for a short period of time under the control of central processing unit 114 to supply a pulse dose of nitric oxide gas in conduit 116 to NO supply line 64. It is also possible, and many times preferred to provide a continuous, proportional NO/N$_2$ gas flow to achieve a desired NO concentration. A flow restrictor 118 is provided at the output of valve 112 and pressure sensor 120 is connected downstream of flow restrictor 118 so that the pressure characteristics existing in conduit 116 may be used to confirm proper operation of valve 112. Dosing means 110 for providing a pulse dose of NO into the breathing gases of the patient is shown in simplified form in FIG. 3 and may incorporate further features of such a device such as those shown in U.S. Pat. Nos. 6,089,229; 6,109,260; 6,125,846; 6,164,276; and 6,581,592.

To control the operation of valve 112, central processing unit 114 receives settings from gas delivery system 10 in conductor 122 as well as operating signals in conductor 124 indicating that gas delivery system 10 is providing inspiratory breathing gases in inspiratory limb 26. For example, the signal in conductor 124 may comprise a signal from inspiratory flow sensor 38 in gas delivery system 10. Alternatively, central processing unit 114 could receive inspiratory gas flow information from injector element 75. This would allow controlled NO delivery while the module is not connected to an equipment rack. Central processing unit 114 provides operating data to gas delivery system 10 in conductor 126.

A gas analyzer 128 is connected to sampling line 72 via conduit 130. Gas analyzer 128 receives setting information from breathing gas delivery system 10 in conductor 132 for selecting the gases to be analyzed, typically NO, nitrogen dioxide, and oxygen, as well as alarm limits for the monitored gases. Gas analyzer 128 provides monitoring data in conductor 134 to breathing gas delivery system 10. Gas analyzer 128 is also connected to alarm 136 for providing visual or audible alarms in the event the gas analysis data goes beyond an established alarm limit. The alarm data may also be provided to gas delivery system 10 in conductor 138.

Modular NO delivery device 50 may be powered by a connection to power mains via gas delivery system 10 and a connector on the rear of the NO delivery module to provide line power to power feed 140. Or, the NO delivery module may be powered by an internal battery 142. Switches 144 and 146 allow connection of the appropriate power source as well as allowing battery 142 to be charged from the power in power feed 140.

In use, modular NO delivery device 50 is inserted in modular equipment bay rack 40 of a gas delivery system 10 at one location, such as an intensive care unit. Injection element 62, sampling port 68 and the flow sensor port are connected in inspiratory limb 26 by appropriate connectors. NO supply conduit 56 is connected to a source of NO 60 and to port 54.

The desired operating parameters for gas delivery system 10 are entered in user interface 14. The NO dosage amounts are similarly entered in interface 14 and provided to central processing unit 114 in NO delivery module 50 in conductor 122.

Operation of gas delivery system 10 and NO delivery module 50 then commences. In the NO delivery module, central processing unit 114 operates valve 112 to provide continuous or pulsatile doses of NO to injector element 62 in NO supply line 64 in synchronism with the supply of breathing gases in inspiratory limb 62 via signals provided in conductor 124. Gas analyzer 128 samples the breathing gases provided to the patient via sampling line 72 to provide monitoring data in conductor 134 and to operate alarm 136 if necessary.

When it is desired to transport patient 12 from a first location, such as an intensive care unit, to another location, such as a hospital room, the supply of breathing gases to patient 12 will be switched from a gas delivery device 10 to another gas delivery device, such as a transport ventilator. This is typically carried out by disconnecting inspiratory limb 26 and expiratory limb 34 from gas delivery system 10 and connecting them to appropriate ports on the transport ventilator. NO delivery module 50 is removed from rack 40 of the gas delivery device 10 at the first location. It can be inserted in a corresponding modular equipment bay in the transport ventilator. Or, a connection cable may be provided between the transport ventilator and NO delivery module 50. The connection provides the data in conductor 124 necessary to synchronize the supply of NO with the supply of breathing gases by the ventilator. Module 50 may be switched to operation from battery 142. If desired, nitric oxide supply 60 may be disconnected and valve 108 operated to supply nitric oxide gas from the transport supply 106 in module 50. The connection to the transport ventilator may also permit monitoring information in conductors 126 and 134 to be provided to the transport monitor.

Central processing unit 114 maintains the operating parameters and NO dosage settings entered via user interface of the breathing gas delivery system at the first location as the patient is being transported.

Following completion of the patient transport, at the new location, the procedures carried out at the first location are essentially reversed. That is, patient 12 is disconnected from the transport gas delivery system 10 and placed on the gas delivery system 10 at the new location.

NO delivery module 50 is inserted in the modular equipment bay rack 40 of the gas delivery system 10 at the new location. The supply of power to module 50 reverts to line power provided in power feed 140. If NO supply 60 has not been transported with the patient, NO supply line 56 is connected to a source 60 at the new location and valve 108 is operated to terminate NO supply from source 106 and commence NO supply from NO supply line 56 and conduit 104. Central processing unit 114 and gas analyzer 128 are connected to the gas delivery system 10 at the new location to maintain the supply of continuous or pulsatile doses of NO in NO delivery line 64 and injection module 75. Information from the analysis of the breathing gases by gas analyzer 128 is also provided to gas delivery system 10 at the new location.

It will be appreciated that the embodiment of the invention shown in FIG. 3 may be used with a variety of ventilators manufactured by different manufacturers inasmuch as all the elements necessary for delivery of NO are contained in the module. This provides flexibility in the use of the NO delivery module.

Figure 4:
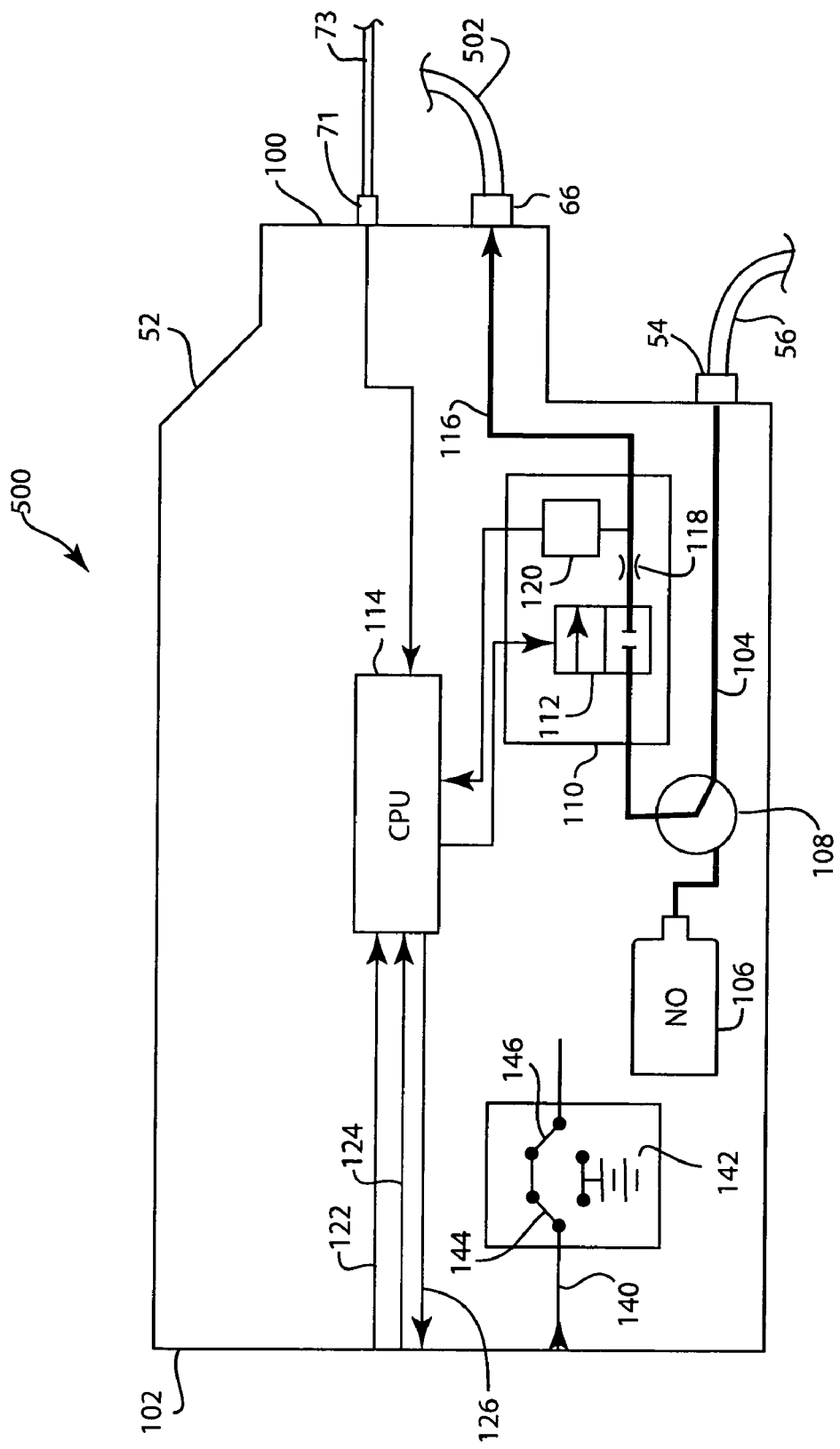
FIG. 4 is a generally schematic showing of the construction of another embodiment of the modular NO delivery device.

FIG. 4 shows another embodiment of a NO delivery module as module 500. Module 500 is simpler in construction than module 50 but is correspondingly more integrated with a particular breathing gas delivery system with which it is designed to be used. Hence, with the NO delivery module of FIG. 4 the gain is simplicity over that of FIG. 3 but the trade-off is somewhat less flexibility for use with a variety of different types of breathing gas delivery systems. In FIG. 4, elements corresponding to those of FIG. 3 bear the same reference numerals.

In the application contemplated for NO delivery module 500, the various gas monitoring and alarming functions are provided by the breathing gas delivery system rather than the NO delivery module. Hence, gas analyzer 128, alarm 136, and the related circuitry is omitted.

The portions of the module providing a continuous or pulsatile dose of NO remain generally the same. However, the nitric oxide dosage provided in conduit 116 at port 66 is provided to a supply conduit 502 that is connected to the breathing gas delivery system so that the NO dose is supplied to the breathing gases in the gas delivery system, such as a mechanical ventilator, rather than in the inspiratory limb of the breathing circuit.

Various alternatives and embodiments are contemplated as being within the scope of the following claims particularly pointing out and distinctly claiming the subject matter regarded as the invention.

What is claimed is:

1. A modular nitric oxide (NO) delivery device for selectively controlling a flow of NO therapy gas to a patient, the modular NO delivery device comprising: a housing having NO supply port, NO delivery port, and a conduit pneumatically connected to the NO supply port and the NO delivery port, wherein the modular NO delivery device is removably connected to a gas delivery system and is separately coupled to an inspiratory limb of a breathing circuit; a selector valve positioned in the conduit and selectively movable between a first position wherein the NO supply port is pneumatically connected to the NO delivery port and a second position wherein the NO supply port is pneumatically connected to a temporary supply of NO; a controller arranged to control the movement of the selector valve between the first and second positions wherein when the modular NO delivery device is coupled with the NO delivery port, the controller switches the selector valve to the first position, and when the modular NO delivery device is not coupled with the NO delivery port, the controller switches the selector to the second position; and the housing further having a power supply port, a temporary power source and a switch being selectively movable between a first position wherein power is provided to the NO delivery device via the power supply port and a second position wherein power is provided to the device from the temporary power source.

2. The modular NO delivery device of claim 1, further comprising means for providing a pulse dose of NO to the NO supply port.

3. The modular NO delivery device of claim 2, wherein the means for providing a pulse dose comprises a flow control valve.

4. The modular NO delivery device of claim 1, further comprising a gas analyzer pneumatically connected to a sampling port on the housing, the gas analyzer arranged to sample at least one of gas provided to the patient and received from the patient.

5. The modular NO delivery device of claim 4, wherein the gas analyzer receives setting information from an external control mechanism via a conductor.

6. The modular NO delivery device of claim 5, further comprising an alarm for providing an indication that gas analyzed by the gas analyzer obtains a value outside predetermined value limits.

7. The modular NO delivery device of claim 1, wherein the controller is contained within the housing.

8. The modular NO delivery device of claim 7, wherein the controller is in communication with an external control mechanism via a conductor.

9. The modular NO delivery device of claim 1, wherein the temporary power source is contained within the housing.

10. The modular NO delivery device of claim 1, wherein the temporary power source is a battery.

11. The modular NO delivery device of claim 1, wherein the temporary supply of NO is contained within the housing.

12. The modular NO delivery device of claim 1, wherein when the modular NO delivery device is disconnected from the gas delivery system, the selector valve is automatically moved into the second position.

13. The modular NO delivery device of claim 1, wherein when the modular NO delivery device is disconnected from the gas delivery system, the switch is automatically moved into the second position.

14. The modular NO delivery device of claim 1, wherein when the modular NO delivery device is connected to the gas delivery system, the selector valve is automatically moved into the first position.

15. The modular NO delivery device of claim 1, wherein when the modular NO delivery device is connected to the gas delivery system, the switch is automatically moved into the first position.

16. The modular NO delivery device of claim 1, further comprising means for providing a continuous dose of NO to the NO delivery port.

17. The modular NO delivery device of claim 16, wherein the means for providing a continuous dose comprises a flow control valve.

* * * * *